United States Patent [19]
McNeal et al.

[11] Patent Number: 4,889,613
[45] Date of Patent: Dec. 26, 1989

[54] ANALYTICAL APPARATUS, ELECTRODE AND SAMPLE CONTAINER FOR USE THEREWITH

[75] Inventors: Jack D. McNeal, Long Beach; Mark Levine, Irvine; J. Harvey Beery, La Habra, all of Calif.

[73] Assignee: Beckman Instruments, Inc., Fullerton, Calif.

[21] Appl. No.: 96,099

[22] Filed: Sep. 11, 1987

[51] Int. Cl.[4] .................... G01N 27/28; G01N 27/30
[52] U.S. Cl. .................... 204/416; 74/54; 74/57; 204/400; 204/414; 204/435; 422/63; 422/67; 422/68; 422/99; 422/102
[58] Field of Search ............. 204/412, 416, 414, 435, 204/400, 418, 419, 420, 401; 422/63, 67, 68.06, 99, 102; 435/291; 74/54, 57

[56] References Cited

U.S. PATENT DOCUMENTS

| | | | |
|---|---|---|---|
| 4,020,830 | 5/1977 | Johnson et al. | 128/635 |
| 4,053,381 | 10/1977 | Hamblen et al. | 204/416 |
| 4,133,735 | 1/1979 | Afromowitz | 204/406 |
| 4,171,246 | 10/1979 | Hamblen et al. | 204/1 T |
| 4,184,936 | 1/1980 | Paul et al. | 204/400 |
| 4,225,410 | 9/1980 | Pace | 204/412 |
| 4,257,862 | 3/1981 | Schnipelsky et al. | 204/400 |
| 4,321,122 | 3/1982 | Whitcomb et al. | 204/400 |
| 4,454,007 | 6/1984 | Pace | 204/1 T |
| 4,468,271 | 8/1984 | Pierson | 156/220 |
| 4,512,852 | 4/1985 | Tsuboshima et al. | 204/1 T |
| 4,556,474 | 12/1985 | Pierson | 204/416 |
| 4,568,445 | 2/1986 | Cates et al. | 204/415 |
| 4,613,422 | 9/1986 | Lauks | 204/419 |
| 4,654,127 | 3/1987 | Baker et al. | 204/1 T |
| 4,713,165 | 12/1987 | Conover et al. | 204/403 |
| 4,735,778 | 4/1988 | Maruyama et al. | 422/102 |

FOREIGN PATENT DOCUMENTS

| | | |
|---|---|---|
| 0142226 | 5/1985 | European Pat. Off. . |
| 0230645 | 8/1987 | European Pat. Off. . |
| 8700286 | 1/1987 | Int'l Pat. Institute . |
| 2136145 | 9/1984 | United Kingdom .............. 74/57 |

OTHER PUBLICATIONS

Research Disclosure, No. 190, 19040, Feb. 1980.

Primary Examiner—G. L. Kaplan
Attorney, Agent, or Firm—William H. May; Arnold Grant; Gary T. Hampson

[57] ABSTRACT

An analysis system including an ion selective electrode assembly, a sample container and a transport mechanism. The electrode assembly includes a reference electrode within a reference gel-filled well and ion selective electrodes disposed on an elongated portion of the electrode assembly. The sample container includes a body defining a plurality of reservoirs and a slot retaining an absorbant wiping and/or blotting material. The electrode assembly may be removably fixed relative to the transport mechanism. The transport mechanism includes a support table adapted to receive the sample container. The support table moves relative to the electrode assembly under the control of a cam to sequentially position the elongated portion of the electrode assembly within the reservoirs and the slot of the sample container.

35 Claims, 6 Drawing Sheets

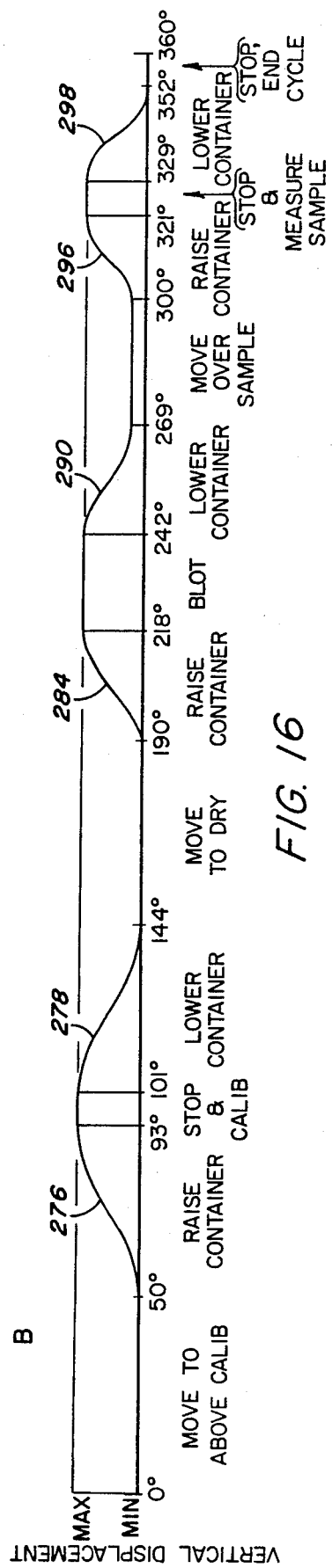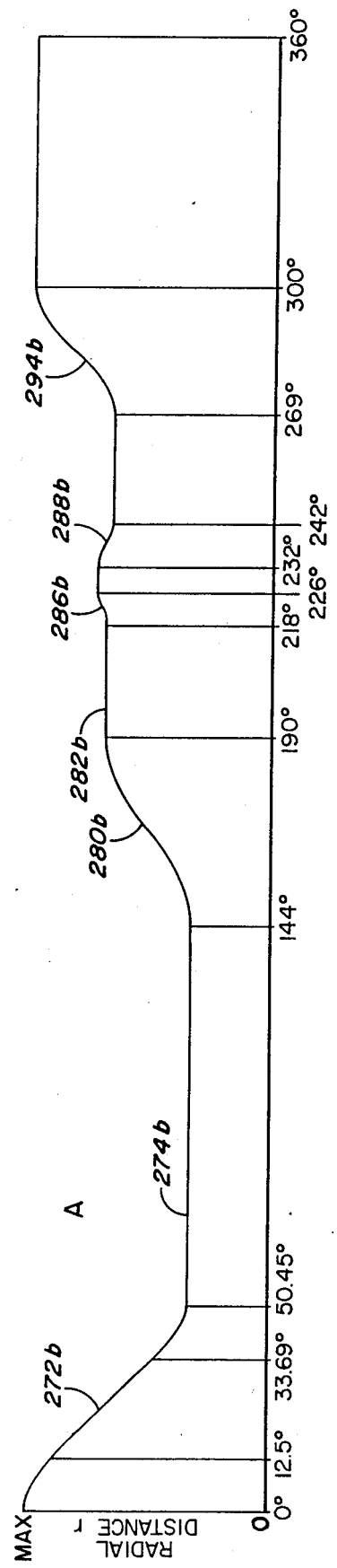
FIG. 16
FIG. 15

ANALYTICAL APPARATUS, ELECTRODE AND SAMPLE CONTAINER FOR USE THEREWITH

FIELD OF THE INVENTION

The present invention relates generally to the field of analytical systems and more particularly to low-cost clinical analytical systems including instruments, ion selective electrodes and sample containers for use therewith.

BACKGROUND OF THE INVENTION

Electrochemistry has been widely used for the measurement of various analytes in blood samples. In an electrochemical system, ion selective or sensing electrodes particularly sensitive to, for example, sodium, potassium, chloride, lithium or calcium ions are exposed to a patient sample. The electrical activity detected by the ion selective electrodes is proportional to the concentration of the corresponding analytes, yielding rapid, accurate and repeatable determinations of analyte concentrations.

A system marketed by the Eastman Kodak Company under the trademark Ektachem Model DT-60 utilizes a single use carrier or cassette employing ion selective electrodes for the measurement of the electrolytes in serum or plasma. The Kodak system requires the simultaneous pipetting of both sample and calibrator onto two separate sections of the cassette. The system measures the potential difference between the calibrator and sample to yield a measurement of an electrolyte in the sample. Although the Kodak system performs adequately, utilizing a single-use disposable cassette, the cassettes must be used on an analyzer that is itself both complex and expensive. Furthermore, because the system measures a potential difference between two sections of the cassette, each of the sections on any given cassette must perform exactly the same. This requirement presents a manufacturing challenge and can increase the cost of manufacturing and quality control.

Another approach to the measurement of electrolytes using ion selective electrodes is a system developed and marketed by SenTech Medical Corporation, now owned by Johnson and Johnson. The SenTech system employs a single-use plastic sensor card which carries several ion selective electrodes suitable for measuring, for example, calcium, sodium, and chloride as well as sample pH. A reservoir carried by the card includes a chamber containing a calibrator fluid and an empty chamber which receives a patient sample. In use, the patient sample is added to the reservoir and the card is inserted into an analyzer. The reservoir is rotated to a calibration position, allowing calibrator fluid to flow across the ion selective electrodes and providing a calibration value for the analyzer for each of the electrodes. Once the calibration values have stabilized and are recorded by the analyzer, the reservoir is rotated further to allow the sample to flow across the electrodes. The flow of sample is used to clear the calibrator fluid from the electrode surfaces and to present sample to the electrodes for measurement.

Unfortunately, the SenTech system requires the fabrication of a number of parts which then must be assembled into the completed cards, making each of the sensor cards expensive and increasing the cost per test. The calibrator/sample reservoir must be manually rotated in response to prompts from the instrument, thus requiring operator attention during the analysis. Also, because the flow of sample is used to clear the calibrator fluid from the electrode surfaces, calibrator contamination is possible if sample flow is uneven or includes entrained gas bubbles.

Thus, there is a need for a simple and inexpensive electrochemical system for the measurement of electrolytes or other analytes measurable with ion-selective electrodes. There is also a need for a system using an inexpensive analyzer and correspondingly inexpensive electrodes. Preferably, such a system should be completely automatic once the analyzer is loaded with the appropriate electrode and with a patient sample so that an operator need merely start the analysis cycle and may then attend to other matters while the analysis is performed.

SUMMARY OF THE INVENTION

The present invention overcomes the limitations and drawbacks described above, providing an inexpensive, simple yet automatic analyzer which uses inexpensive and simple electrode assemblies. The electrode assemblies are particularly adaptable to mass production techniques, reducing electrode cost and thus cost-per-test.

An electrode assembly in accordance with the present invention includes a nonconductive substrate upon which conductors are deposited, printed or otherwise applied. The conductors include contact areas as well as base areas upon which are deposited a reference electrode and ion selective electrodes. The reference electrode is disposed in an enclosed well which contains a reference gel to provide a reference potential to the reference electrode. The electrode assembly may further include an elongated portion upon which the ion selective electrodes are disposed. For shipment, the elongated portion may be removably inserted into a sleeve. The sleeve includes a conditioning gel which is placed in removable contact with the ion sensing electrodes to condition the electrodes during storage and shipment.

A sample container or cup in accordance with the present invention comprises a sample reservoir, a calibrator reservoir and a slot which retains absorbant material disposed between the sample and calibration reservoirs. The sample reservoir may take the form of a first reservoir and a second larger reservoir with a notch bridging the two to allow for fluid flow therebetween. Also, the calibrator reservoir may be filled with a suitable calibrator reagent and closed with a seal or cover. The seal or cover is either pierced or peeled away to expose the calibrator reagent. A handle formed at one end of the sample container provides for convenient handling by a user.

The electrode assembly and sample container are both particularly adapted for use with a simple and inexpensive transport mechanism. The mechanism includes a support table which supports the sample container. The support table is in turn supported by a pivot and a cam follower. The cam follower rides against and follows a groove carried by a rotatable cam. The electrode assembly is held in a fixed position with respect to the transport mechanism by a support that also provides electrical contact with the conductors on the electrode assembly.

One complete rotation of the cam moves the support table and the sample container with respect to the stationary electrode assembly so as to perform an analysis of a sample contained in the sample container. The motion of the sample table first moves the sample container to immerse the elongated portion, including the electrodes disposed thereon, in the calibrator reagent. The sample container is lowered, moved horizontally and raised to remove the elongated portion from the calibrator reagent and reposition the sample container with the elongated portion within the slot. Calibrator reagent is wiped from the elongated portion onto the absorbant material retained within the slot. The sample container is again displaced vertically and horizontally to position the elongated portion in the sample reservoir for sample measurement. After the sample measurement is completed, the support table returns the sample container to its starting position. The cam may be driven by an inexpensive motor to further simplify the mechanism and reduce its cost.

BRIEF DESCRIPTION OF THE DRAWINGS

FIGS. 15 and 16 are diagrammatic representations of the radial and vertical displacements programmed by the cam of FIG. 14.

DETAILED DESCRIPTION OF THE INVENTION

Figure 1:
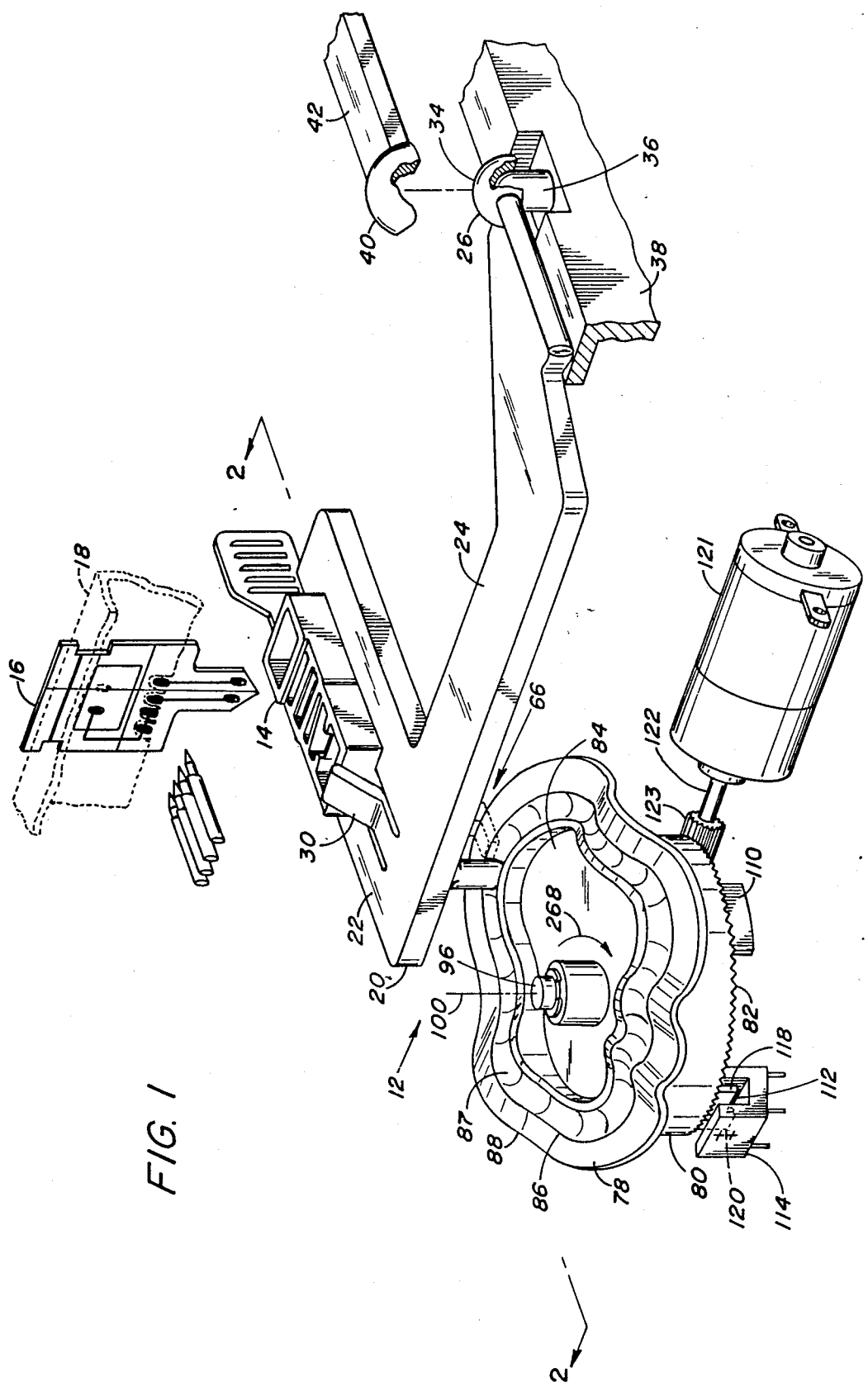
FIG. 1 is a perspective view of an electrode assembly, sample container and transport mechanism in accordance with the present invention.
Figure 2:
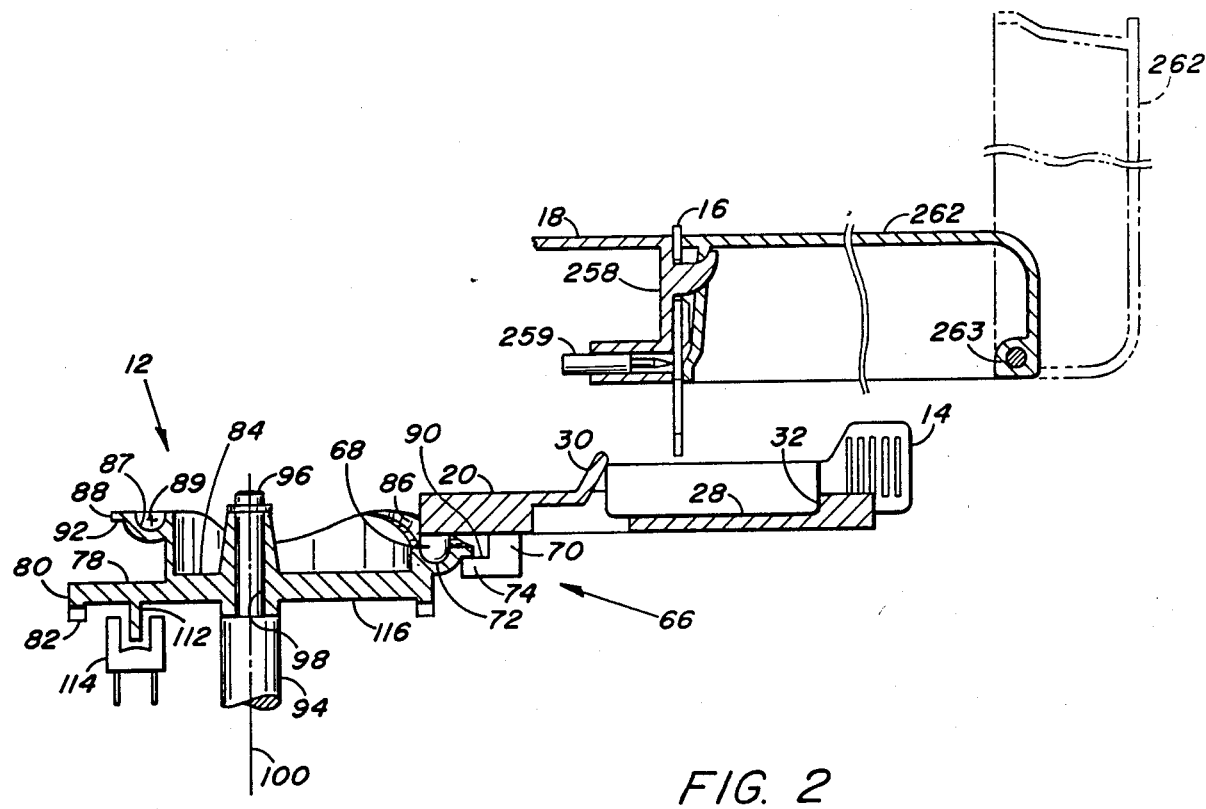
FIG. 2 is a section view of the mechanism of FIG. 1 taken along line 2—2 thereof.

With reference to FIGS. 1 and 2, the present invention is directed to a transport mechanism 12, a sample container 14, an electrode assembly 16 and an electrode assembly support 18. Briefly, the transport mechanism 12 supports and moves the sample container 14 both horizontally and vertically with respect to the electrode assembly 16 held stationary in the support 18. The sample container 14 is moved so as to expose the electrode assembly 16 to a calibrator, to wipe the calibrator from the electrode assembly 16, and to expose the electrode assembly 16 to a sample. The electrode assembly 16 and sample container 14 may then be replaced for a next sample analysis cycle.

Returning to the transport mechanism 12, a pivoted support table 20 includes a rectangular portion 22 that supports the sample container 14. An arm 24 is integrally formed with the rectangular portion 22 and is supported at a free end by means of a pivot 26. The rectangular portion 22 includes a depression 28 sized to receive and retain the sample container 14. An integrally formed spring member 30 urges the sample container 14 into engagement with an end 32 of the depression 28 to thus accurately register the sample container 14 with respect to the support table 20.

The pivot 26 in the embodiment disclosed herein is in the form of a ball and trunion. The pivot 26 includes a hemispherical socket 34 which is received and supported by a spherically radiused surface of a pin 36. The pin 36 is in turn supported by a frame member 38 of, for example, an analyzer (not shown) utilizing the present invention. The socket 34 is retained on the pin 36 by means of a cap 40, shown removed from the socket 34 in FIG. 1 for clarity. The cap 40 urges the socket 34 into engagement with the pin 36, enabling the support table 20 to be pivoted horizontally and vertically about the pivot 26. The cap 40 may also be formed, for example, as a portion of another frame member 42 of an analyzer utilizing the present invention.

The support table 20 also includes a cam follower 66 in the form of a pin 68 and a retainer 70. The cam follower 66 is formed at an end of the rectangular portion 22 and near the intersection of the rectangular portion 22 and the arm 24. The pin 68 includes a spherically radiused lower surface 72 and the retainer 70 includes an arm 74 directed toward the pin 68.

The support table 20 is displaced horizontally and vertically by a cam 78. The cam 78 includes a base in the form of a gear 80 having depending teeth 82 about the periphery thereof. An upper portion of the cam 78 is in the form of a body 84 which defines a curvilinear groove 86. A bottom portion 87 of the groove 86 is radiused to match the radius of the surface 72. A lip 88 is formed proximate the groove 86 and is spaced a predetermined constant distance from a center line 89 of the groove 86 to thus parallel the groove 86. As is shown in FIGS. 1 and 2, the pin 68 is sized to be carried by the groove 86 and the upper surface of the arm 74 is adapted to ride against the lower surface of the lip 88. Preferably, a slightly radiused upper surface 90 of the arm 74 presses against a lower surface 92 of the lip 88 to urge the surface 72 of the pin 68 into contact with the bottom portion 87 of the groove 86 so that the pin 68 will accurately reproduce the path described by the center line 89.

The cam 78 is turnably supported on a base 94 by means of a shaft 96 that is retained within a central opening 98 formed in the cam 78. The opening 98 is coaxially aligned with the gear 80 of the cam 78, and defines a central vertical axis 100 of the cam 78. The path of the center line 89 with respect to the axis 100 is described hereinbelow with reference to FIGS. 14 and 15.

The rotational position of the cam 78 about the shaft 96 is detected by flags 110, 112 in cooperation with an optical detector 114. The optical detector 114 is a two-level type detector, including upper and lower detectors each comprising a light source such as a light emitting diode and a photo detector. Both of the flags 110, 112 are fixed to and rotate with a lower surface 116 of the gear 80. The flag 110 is of a height to interrupt only the upper optical path in the detector 114. Flag 112, however, comprises a first portion 118 which interrupts only the upper optical path of the detector 114 and a second portion 120 of sufficient height to interrupt both of the detector 114 optical paths. Thus, two unambiguous conditions may be detected by the optical detector 114, enabling the flags 110, 112 and detector 114 to indicate various rotational positions of the cam 78 as well as a home or start position for the cam 78. For example, the flag 110 and the first shorter portion 118 of the cam 112 may be used to detect various rotational positions of the cam 78 and the second longer portion 120 may be used to detect a home or start position for the cam 78.

The cam 78 is driven by means of a gear motor 121. The gear motor 121 includes a shaft 122 which supports a pinion gear 123. The pinion gear 123 is engaged with the teeth 82 of the gear 80 to provide rotation of the cam 78 and corresponding displacement of the support table 20 as is described below with reference to FIGS. 14 and 15.

The support table 20 and cam 78 may be formed in any conventional fashion. As an example, both the support table 20 and cam 78 may be injection molded. One of these parts may be molded from acetal resin and the other from nylon resin to enhance wear resistance and reduce friction between the parts.

Figure 3:
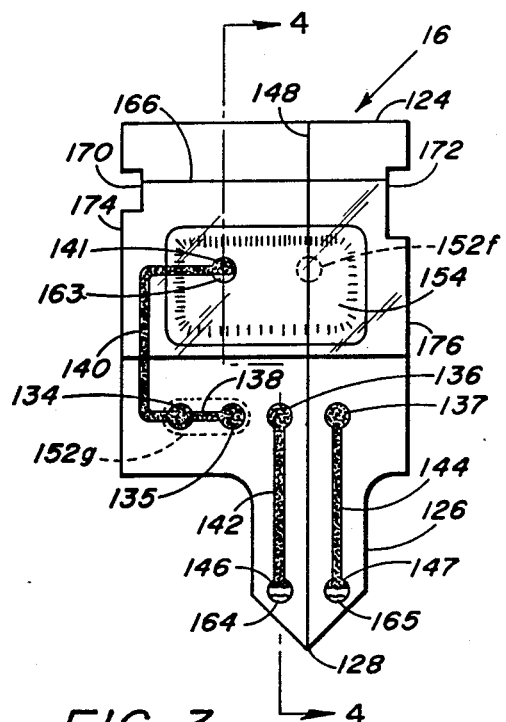
FIG. 3 is a front view of the electrode assembly of FIGS. 1 and 2.
Figure 6:
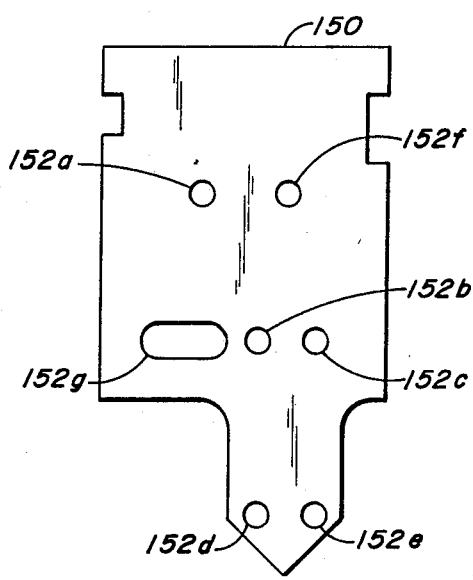
FIG. 6 is a front view of an insulator used in the construction of the electrode assembly of FIG. 3.

With reference now to FIGS. 3-6, the electrode assembly 16 is generally in the form of a rectangular portion 124 and an elongated portion 126. The elongated portion 126 is slightly off-center with respect to the rectangular portion 124 and includes a pointed end 128 at the furthermost extension of the elongated portion 126. As to the structure of electrode assembly 16, the electrode assembly 16 includes a substrate layer 130 formed, for example, from rigid PVC plastic approximately 0.50 mm thick. The substrate layer 1130 is cleaned with, for example, water, glacial acetic acid and ethanol and a thick film polymer conductive ink including, as an example, carbon, is screen printed or deposited by other suitable methods onto the substrate layer 130. As illustrated in FIG. 3, the conductive ink is deposited to define four contact pads 134-137, conductor traces 138, 140, pad 141, conductor traces 142, 144 and pads 146, 147.

More particularly, the four contact pads 134-137 are disposed on the substrate layer 130 approximately midway along the longer overall dimension of the electrode assembly 16. The contact pads 134 and 135 are connected by the conductor trace 138. The conductor trace 140 is directed near the edge of the substrate layer 130 upwardly as illustrated in FIG. 3 and laterally to connect to the pad 141 which receives a reference electrode as is described hereinbelow. Similarly, conductor traces 142 and 144 are formed from the contact pads 136, 137 respectively, parallel to the longer overall dimension of the electrode assembly 16 and downwardly as illustrated in FIG. 3 to the pads 146, 147. The pad 146 is illustrated in enlarged form in FIG. 5.

A thread 148 is placed against the substrate layer 130. The thread may be, for example, a non-mercerized cotton type thread, the purpose of which is described hereinbelow. As seen in FIG. 3, the thread 148 is positioned parallel to the longer dimension of the electrode assembly 16 and is parallel to and essentially midway between the conductor traces 142 and 144.

With the pads 134-137, 141, 146, 147 and conductive traces 138, 140, 142, 144 deposited onto the substrate layer 130, a 0.1 mm thick PVC plastic insulator 150 (FIG. 6) is laminated onto the substrate layer 130 through, for example, a heat lamination process which in particular may be accomplished by a card laminator. The thread 148 is held in place as the insulator 150 is laminated to the substrate layer 130. With the insulator 150 laminated in place, a cross-section of the thread 148 is exposed between the insulator 150 and the substrate layer 130 at the pointed end 128.

The insulator 150 includes openings 152a-152g (FIG. 6) formed therethrough. Each of the openings 152a-152e is aligned with respective pads 141, 136, 137, 146 and 147 and such openings have a slightly larger diameter than their respective pads. The opening 152f is aligned over the thread 148 as seen in FIG. 3 and the elongated opening 152g exposes both of the pads 134 and 135.

Figure 4:
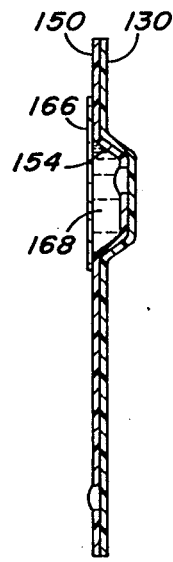
FIG. 4 is a section view of the electrode assembly of FIG. 3 taken along line 4—4 thereof.
Figure 5:
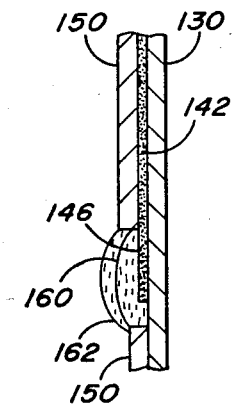
FIG. 5 is an enlarged partial section view of an ion selective electrode carried by the electrode assembly of FIG. 3.
Figure 7:
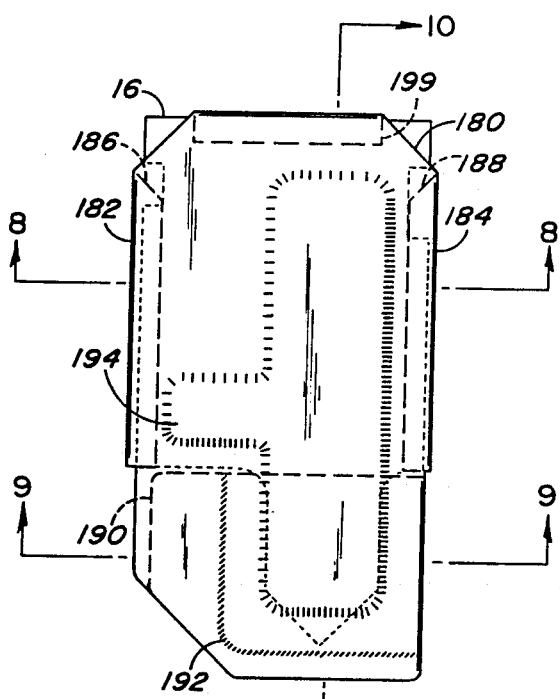
FIG. 7 is a front view of a sleeve or holder suitable for use with the electrode assembly of the present invention.

As illustrated in FIGS. 3 and 4, a depression or tub 154 is formed into the laminated substrate layer 130 and insulator 150. In the embodiment disclosed herein, the volume of the tub 154 is approximately 100 ul. The tub 154 may be formed by either, for example, a cold forming process by pressing the laminated substrate layer 130 and insulator 150 between a die and arbor, or the laminated substrate layer 130 and insulator 150 may be first heated to accomplish a hot-forming process.

The electrode pads 141, 146, 147 are silver plated by immersing the pads 141, 146, 147 in a solution of silver cyanide and the application of a plating current through the solution and pads 141, 146, 147. The plated pads 141, 146 and 147 are washed with the deionized water and the silver plating is then chlorodized by immersing the silver plated pads 141, 146 and 147 into a 0.1 molar potassium chloride solution and passing current through carbon and silver electrodes disposed within the solution in a conventional fashion. Preferably, the pads 141, 146 and 147 are chloridized within one hour of the silver plating to prevent oxidization of the silver deposited upon the pads 141, 146 and 147. The laminated substrate layer 130 and insulator 150 are then washed in deionized water and dried. The chloridized silver plated pad 141 forms a reference electrode 163, shown partially cut away in FIG. 3 to expose the pad 141.

Two layers 160, 162 of sodium ion selective membrane material (shown with exaggerated thickness for clarity in FIG. 5) are applied to the electrode pad 146. Similarly, two layers of potassium ion selective electrode membrane material are applied to the electrode pad 147 to thereby form ion selective sodium and potassium measuring electrodes 164 and 165. The two layers 160, 162 and the two layers of membrane material on the potassium electrode 165 are shown in partial cutaway in FIG. 3 to reveal the pads 146, 147. The membrane materials are not critical to the present invention and may be, for example, a conventional ion selective membrane material made in accordance with techniques well known in the art. Two examples of membrane materials are set forth hereinbelow in Examples 1 and 2.

A length of clear adhesive-backed polyester tape 166 is applied to the insulator 150 over the tub 154, closing the tub 154. A reference gel 168 is injected through the tape 166 into the reservoir defined by the tub 154 and the tape 166. The reference gel 168 may be any suitable gel as is well known in the art and the precise formulation is not critical to the present invention. The reference gel 168 contacts the reference electrode 163 and the thread 148 through the opening 152f. The reference gel 168 tends to saturate the thread 148 via capillary action. An example of the composition of a suitable reference gel 168 is set forth in Example 3 below.

Figure 11:
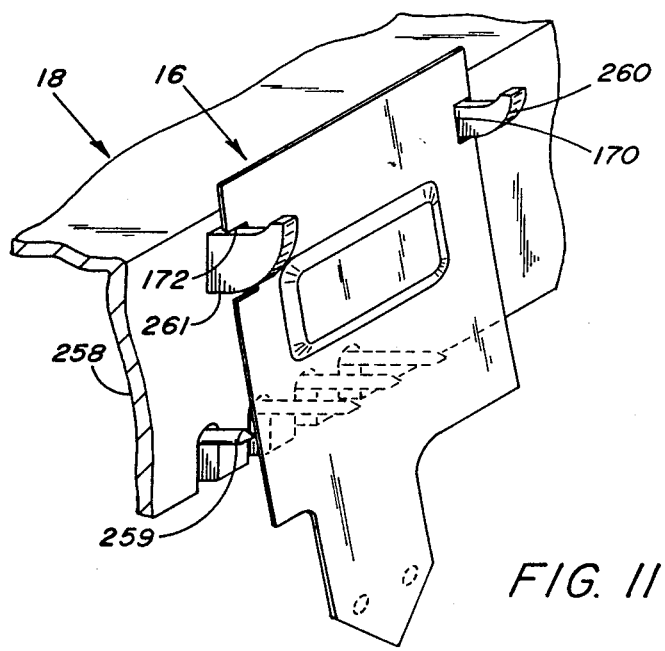
FIG. 11 is an electrode assembly support suitable for use with the transport mechanism of FIG. 1.

Notches 170 and 172 are cut into opposite edges 174 and 176 of the rectangular portion 124 above the tub 154 as illustrated in FIG. 3. The notch 172 is larger than the notch 170 and both notches 170, 172 cooperate with the electrode assembly support 18 (as described below with reference to FIG. 11) such that the electrode assembly 16 will be received by the support 18 in only one orientation with the elongated portion 126 directed downwardly.

Figure 8:
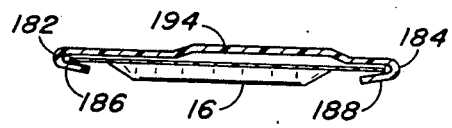
FIG. 8 is a cross section view of the sleeve of FIG. 7 taken along line 8—8 thereof.
Figure 9:
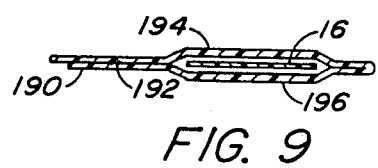
FIG. 9 is a cross-section view of the sleeve of FIG. 7 taken along line 9—9 thereof.
Figure 10:
FIG. 10 is a cross-section view of the sleeve of FIG. 7 taken along line 10—10 thereof.

Before storage and shipment, the electrode assembly 16 is inserted into a sleeve 180 (FIGS. 7-10). The sleeve is formed of a rigid clear plastic material. Side edges 182, 184 are formed by respective tabs 186, 188 that are folded as illustrated in FIG. 8. A tab 190 on a lower portion of the sleeve 180 is folded over and welded to the front of the sleeve 180 along a weld line 192. A portion 194 on the face of the sleeve 180 is raised and a portion of 196 of the tab 190 is similarly raised, defining a reservoir 197 which contains a gel 198.

With the electrode assembly 16 (as shown in phantom in FIGS. 7-10) inserted into the sleeve 180, a top tab 199 is folded over the top of the electrode assembly 16 to retain the electrode assembly 16 within the sleeve 180 for storage and shipment. The sodium and potassium electrodes 164 and 165 contact the gel 198 and remain in contact with the gel 198 until the electrode assembly 16 is removed from the sleeve 180 for use. The gel 198 is an ionic composition similar to a calibrator used with the electrode assembly 16, all as is well known in the art. The gel 198 also tends to wet the thread 148 through its exposed cross section at the pointed end 128 and condition and preserve the electrodes 164, 165 during shipment and storage. The gel 198 preferably uses an agarose base which allows the gel 198 to cleanly separate from the elongated portion 128 when the electrode assembly 16 is removed from the sleeve 180. The raised portion 194 provides clearance between the electrode assembly 16 and the sleeve 180 so that the electrode assembly 16 can be removed from the sleeve 180 without damage to the electrodes 164, 165 and to prevent gel 198 from flowing between the electrode assembly 16 and sleeve 180. An example of the gel 198 composition is set out in Example 4 below.

Advantageously, the structure of the electrode assembly 16 lends itself well to mass or continuous (web) production techniques. For example, the substrate layer 130 and insulator 150 may both initially take the form of blanks such as individual rectangular pieces of material larger than the overall dimensions of the electrode assembly 16 or a continuous web or roll of material. The conductive ink is applied to the substrate layer 130 blank and the openings 152a-152g are formed into the insulator 150 blank. The thread 148 is positioned over the substrate layer 130 blank and the substrate layer 130 blank and the insulator 150 blank are laminated as described above. The laminated substrate layer 130 blank and insulator 150 blank are then die cut to form the outline shown in FIG. 2, which may includes the notches 170, 172. Processing of the electrode assembly 16 may then continue as described above.

Figure 12:
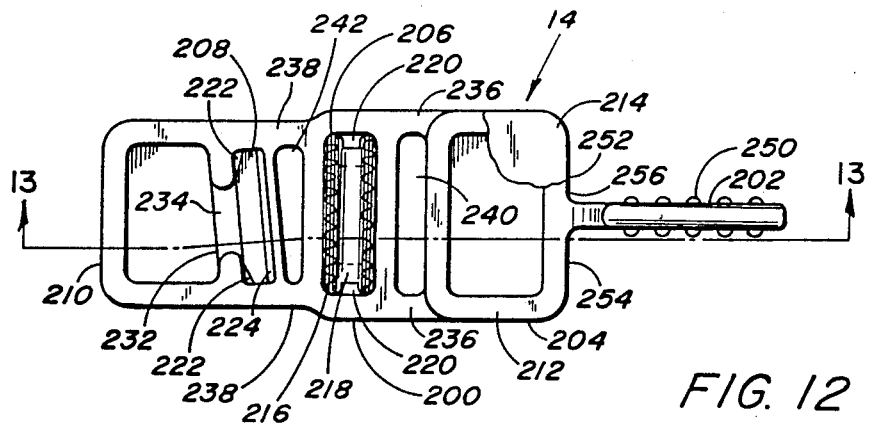
FIG. 12 is a top view of a sample container in accordance with the present invention.
Figure 13:
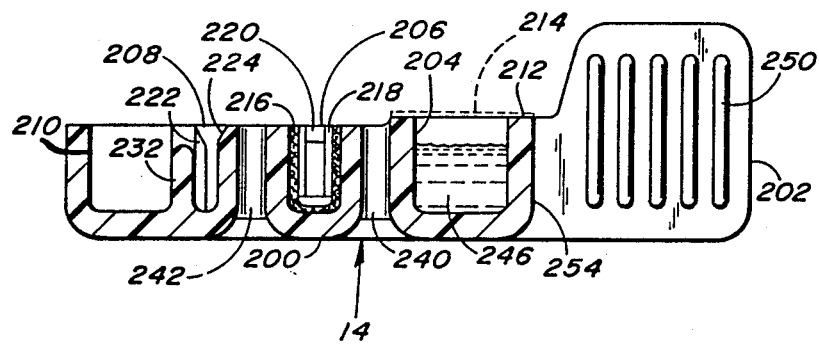
FIG. 13 is a section view of the sample container of FIG. 12 taken along line 13—13 thereof.
Figure 17:
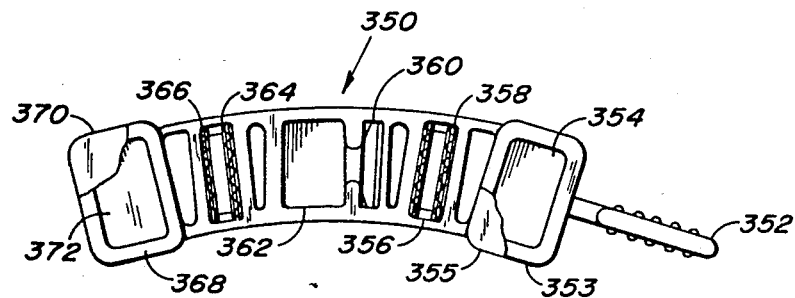
FIG. 17 is a top view of another embodiment of a sample container in accordance with the present invention.

With reference now to FIGS. 12 and 13, the sample container 14 comprises a main body 200 and a handle 202. The main body 200 is generally rectangular in shape and defines a rectangular calibration reservoir 204, a wiping slot 206, a sample reservoir 208 and a sample overflow reservoir 210. Each of the reservoirs 204, 208 and 210 and the slot 206 are open at the top thereof as seen in FIG. 13.

The calibrator reservoir 204 includes a raised upper edge 212 which is adapted to receive a seal 214 shown partially cut-away in FIG. 12 and in phantom in FIG. 13. The seal 214 may be, for example, a foil seal or laminated foil lid stock thermally welded or fixed with adhesive to the edge 212.

The wiping slot 206 is generally rectangular. Disposed therein is a wiping element 216 which may be formed from an absorbant material such as paper towel or filter paper that as been folded and inserted into the slot 206. The wiping element 216 defines a generally elongated U-shaped channel 218 the sides and bottom of which are lined with the wiping element 216 material. Protrusions 220 at either end of the wiping slot 206 serve to retain the wiping element 216 within the slot 206.

The sample reservoir 208 as illustrated in FIG. 12 is angled slightly with respect to the wiping slot 206 to accommodate a slight radial displacement of the support table 20 about the pivot 26 during operation as is described below. The sample reservoir 208 includes generally triangular shaped corner members 222 and an angled surface 224 at the top of the slot 206 and opposite the corner members 222.

The sample reservoir 208 and sample overflow reservoir 210 share a common wall 232. A notch 236 is formed in the wall 232 between the sample reservoir 208 and sample overflow reservoir 210 to define a spillway 234 between the two reservoirs 208, 210.

The main body 200 includes connecting members 236 and 238. The connecting members 236 connect the calibrator reservoir 202 to the wiping slot 206, defining a rectangular opening 240. The connecting members 238 connect the wiping slot 206 to the sample reservoir 208, defining a triangular opening 242.

A calibrator reagent 246 may be retained within the calibrator reservoir 204 by the seal 214. The calibrator 246 may be of any suitable composition to provide calibration points for the electrodes 164, 165, all in a conventional fashion well known in the art.

The handle 202 includes a plurality of ribs 250 on either side thereof so as to assist in grasping and handling the sample container 14. The handle 202 is formed at a side 252 of the calibrator reservoir 204 opposite from the connecting members 236 and is aligned with the longer dimension of the rectangular main body 200. The intersection of the handle 202 and the calibrator reservoir 204 divides the side 252 to form surfaces 254 and 256 adapted to abut the end 32 as described above with reference to FIG. 2.

The electrode assembly support 18 (FIGS. 2 & 11) includes a rail 258 which may be formed integrally, for example, with a case of an analyzer which incorporates the present invention. The rail 258 supports four spring-loaded contacts 259 (shown in exploded form in FIG. 1). Two hangers 260, 261 project from the rail 258. The hanger 260 is sized to fit the notch 170 in the electrode assembly 16 and the hanger 261, larger than the hanger 260, is sized to fit the larger notch 172. The spacing between the hangers 260, 261 is adapted to conform to the dimension between the notches 170, 172 of the electrode assembly 16.

A cover 262 shown in cross section in FIG. 2 is hinged at a hinge 263. The cover 262 may be a portion of a case of an analyzer utilizing the present invention. With the cover 262 in an open position as indicated in phantom in FIG. 2, the electrode assembly 16 may be hung on the hangers 260, 261 (FIG. 11) by engaging the notches 170, 172 with the hangers 260, 261. As thus positioned, the spring-loaded contacts 259 urge the lower portion of the electrode assembly 16 outwardly and away from the rail 258. The cover 262 may be then swung downwardly to its closed position shown in FIG. 2, urging the electrode assembly 16 against the rail 258. The contacts 259 are urged against the contact pads 134-137 with the contacts 259 in turn connected by suitable wiring to potential measuring and analysis circuits (not shown) of a conventional nature.

In use, the cover 262 is opened to reveal the support table 20 and the electrode assembly support 18. The seal 214 may be removed from the calibrator reservoir 204, exposing the calibrator 246. (As an alternative, the seal 214 may be automatically pierced by the electrode assembly 16 during the operation of the invention as is described below.) A patient sample such as blood or blood plasma or serum is pipetted into the sample reservoir 208 with any excess sample flowing over into the sample overflow reservoir 210 through the notch 234. As an alternative, a patient sample may be poured into the overflow reservoir 210 and, as the reservoir 210 fills, patient sample flows through the notch 234 into the sample reservoir 208. The sample container 14 is then placed within the depression 28, compressing the spring member 30 to thereby retain the sample container 14 within the depression 28. The electrode assembly 16 is removed from the sleeve 180 and is installed onto the electrode support 18 as just described. The cover 262 is closed to clamp the electrode assembly 16 firmly against the rail 258 with the electrode assembly 16, including the elongated portion 126, disposed vertically.

Initially, the support table 20 is positioned such that the elongated portion 126 is aligned vertically over the sample reservoir 208 with the width of the elongated portion 126 parallel to the longer dimension of the sample reservoir 208. Once the sample container 14 is in place, as just described, the motor 121 is energized to rotate the cam 78 in a clockwise direction as illustrated by arrow 268 in FIGS. 1 and 14. As the cam 78 rotates, the pin 68 follows the horizontal and vertical displacements described by the groove 86 and lip 88. In doing so, the support table 20 and thus the sample container 14 is first displaced horizontally and then vertically so as to immerse the lower end of the elongated portion 126 into the calibrator 246. If the seal 214 has not been removed from the calibrator reservoir 204, the pointed end 128 pierces the seal 214 as the sample container 14 is raised by the support table 20 toward the elongated portion 126.

With the end of the elongated portion 126 inserted into the calibrator 246, the sodium and potassium measuring electrodes 164, 165 develop electric potentials proportional to sodium and potassium ion concentrations within the calibrator 246. These potentials are measured in a conventional fashion with respect to the potential developed by the reference electrode 163 to establish a calibration point for the electrode assembly 16. A calibration constant for a calibration curve is supplied externally to the measuring apparatus connected to the contacts 259, establishing a calibration relationship required for the measurement of sodium and potassium ion concentrations in the sample, all in a conventional fashion.

The sample container 14 and support table 20 are then displaced vertically and horizontally so as to position the elongated portion 126 within the wiping slot 206, urging the elongated portion 126 against the wiping element 216 to wipe and/or blot calibrator 246 from the surfaces of the elongated portion 126. The sample container 14 and support table 20 are again displaced vertically and horizontally to lastly position the elongated portion 126 within the sample reservoir 208. The corner members 222 and angled surface 224 of the sample reservoir 208 guide the elongated portion 126 into the sample reservoir 208 as the sample container 14 is raised toward the elongated portion 126 such that the ion sensing electrodes 164, 165 are kept separated from the side wall of the sample reservoir 208. As so positioned within the sample contained in the sample reservoir 208, the sodium and potassium electrodes 164, 165 develop an electrical potential proportional to the concentration of sodium and potassium ions in the sample. The potentials are compared to the potential developed by the reference electrode 163 to determine sodium and potassium ion concentrations as is well known in the art.

With the measurement of the sample completed, the sample container 14 and support table 20 are again displaced vertically to the stop position, that is, the same position as the initial position described above. The cover 262 is opened and the electrode assembly 16 and sample container 14 may then be removed from the mechanism 12 and discarded.

The thread 148 is saturated with reference gel 168 and the conditioning and preserving gel 198 to form an ionic salt bridge or conductor. With the elongated portion 126 positioned in a fluid such as the calibrator 246 or a sample as just described, the thread 148 provides an electron flow path between the sodium and potassium measuring electrodes 164, 165 and the reference electrode 163.

Figure 14:
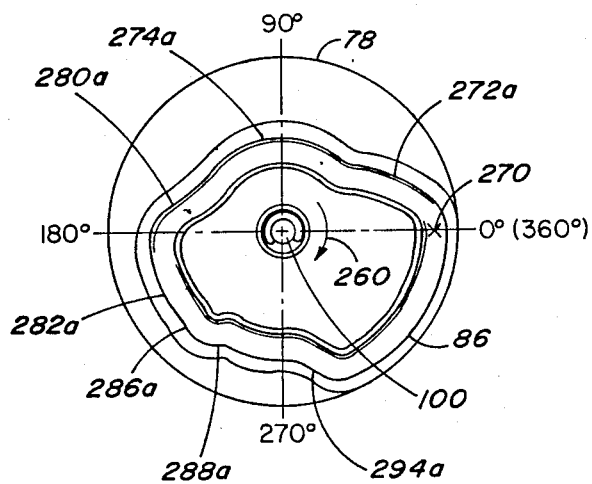
FIG. 14 is a plan view of a cam included in the transport mechanism of FIGS. 1 and 2.

The measurement cycle programmed by the cam 78 is more clearly illustrated with reference to FIGS. 14 and 15. FIG. 14 illustrates a top view of the cam 78, showing in particular the radial distance of the groove 86 from the vertical axis 100 of the cam 78. The radial distance r of the center line 89 from the axis 100 is illustrated by curve A of FIG. 15. Similarly, the center line 89 vertical displacement with respect to an initial 0° position 270 (FIG. 14) is illustrated by curve B of FIG. 15.

In the initial position 270, the cam 78 and pin 68 position the sample container 14 and support table 20 as described above, namely, with the sample container 14 and support table 20 in their lowermost position and with the elongated portion 126 aligned with the sample reservoir 208. With reference to curves A and B of FIG. 15, as the cam 78 rotates clockwise from the initial position 270 (0°) to about 50° of cam 78 rotation, the groove center line 89 is displaced radially inwardly as illustrated by groove portion 272a (FIG. 14) and corresponding curve A segment 272b (FIG. 15). As the pin 68 follows the groove 86, the support table 20 and sample container 14 are drawn toward the axis 100, positioning the calibrator reservoir 204 beneath the elongated portion 126.

From approximately 50° to 144° of cam 78 rotation, the groove 86 center line remains at the same radial distance from the axis 100 as illustrated by groove portion 274a and curve A segment 274b. From approximately 50° to 93° of cam 78 rotation, however, the center line 89 is displaced vertically upwardly as illustrated by curve B segment 276, thus raising the support table 20 and sample container 14 such that the elongated portion 126 is inserted into the calibrator 246 held within the calibrator reservoir 204. Between 93° and 101° of cam 78 rotation, the motor 121 is de-energized, stopping cam 78 rotation and allowing the elongated portion 126 to pause within the calibrator 246. Once the measuring circuitry (not shown) connected via the contacts 259 to the electrodes 163–165 determines that calibration values have been obtained, the motor 121 is again energized. The groove center line 89 is displaced vertically downwardly as illustrated by curve B segment 278. Accordingly, the support table 20 and sample container 14 are displaced downwardly, lowering the sample container 14 away from the elongated portion 126.

At approximately 144° of cam 78 rotation, the vertical displacement is completed and a radial displacement outwardly commences as illustrated by groove portion 280a and curve B segment 280b. Once the radial displacement is completed as illustrated by groove portion 282a and curve A segment 282b, the elongated portion 126 is aligned with the wiping slot 206. Beginning at approximately 190° of cam 78 rotation, the groove centerline 89 is again displaced upwardly as illustrated by curve B segment 284. The support table 20 and sample container 14 are raised to position the elongated portion 126 within the wiping slot 206 and, more particularly, within the wiping element 216.

From approximately 218° to 242° of cam 78 rotation, the groove centerline 89 is displaced radially slightly outwardly and inwardly as illustrated by groove portions 286a and 288a and curve A segments 286b and 288b. The elongated portion 126 is pressed against one surface of the wiping element 216 and then the other surface of the wiping element 216, blotting calibrator 246 from both sides of the elongated portion 126.

With the blotting operation completed, the groove centerline 89 is displaced vertically downwardly as illustrated by curve B segment 290 to thereby withdraw the elongated portion 126 from the wiping slot 206 and simultaneously wiping the back surface of the elongated portion 126. The vertical displacement is slightly less than the displacements illustrated by curve B segments 276, 278 and 284 to save time and unnecessary motion. The slightly less vertical displacement is possible because the pointed end 128 of the elongated portion 126 need not clear the raised edge 212 around the calibrator reservoir 204.

Beginning at approximately 269 degrees of cam 78 rotation, the groove centerline 89 is displaced radially outwardly to thereby move the support table 20 and sample container 14 so as to position the sample reservoir 208 in alignment with the elongated portion 126. The radial displacement of the grove centerline 89 is illustrated by groove portion 294a and curve A segment 294b. The angled relationship of the sample reservoir 208 with respect to the calibrator reservoir 204 and wiping slot 206 accommodates the slight angular displacement of the support table 20 as it pivots about the pivot 26 while following the groove 86.

With the support table 20 and sample container 14 so positioned, the groove centerline 89 is again displaced vertically upwardly as illustrated by curve B segment 296 so as to dip the elongated portion 126 into the sample contained within the sample reservoir 208. The volume displaced by the elongated portion 126 is allowed to overflow through the notch 234 into the sample overflow reservoir 210. With the elongated portion 126 positioned within the sample reservoir 208, the motor 121 is de-energized with cam 78 rotation between approximately 321° and 329°. The pause allows the sodium and potassium measuring electrodes 164 and 165 to reach equilibrium and the measuring circuits to measure the potential developed by such electrodes as described above.

Once the measuring circuits determine that equilibrium has been attained and suitable potential values obtained, the motor 121 is again energized. Beginning at approximately 329°. of cam 78 rotation, the groove centerline 89 is displaced vertically downwardly as illustrated by curve B segment 298 to withdraw the elongated portion 126 from the sample reservoir 208.

Upon completing 352° of cam 78 rotation, the motor 121 continues with the cam 78 coming to rest essentially in the initial or 0° position 270 at which point the motor is de-energized. Thus, the transport mechanism 12 may be reset for a next analysis by removing and replacing the electrode assembly 16 and sample container 14. In the embodiment disclosed herein, a complete cycle represented by a full 360° rotation of the cam 78 may be accomplished in approximately two minutes.

Various modifications to the present invention are possible. For example, the sample container 14 may be modified to add an additional reservoir. With reference to FIG. 16, such an expanded sample container 350 includes a handle 352, calibrator reservoir 353, calibrator 354, seal 355, wiping slot 356, wiping element 358, sample reservoir 360, and sample overflow reservoir 362 similar to the handle 202, calibrator reservoir 204, calibrator 246, seal 214, wiping slot 206, wiping element 216, sample reservoir 208 and sample overflow reservoir 210, respectively, of the sample container 14.

The sample container 350 additionally includes a second wiping slot 364 and a second wiping element 366 retained therein similar to the slot 356 and element 358. A control reagent reservoir 368 is similar to the calibrator reservoir 354 and includes a seal 370 similar to the seal 355. A control reagent 372 is contained within the reservoir 368 in a similar fashion to the calibrator fluid 354 contained within the reservoir 353. The control reagent 372 is formulated in a conventional fashion to provide a test of the performance of the electrode assembly 16 in a manner otherwise well-known in the art.

In use, a sample is added to the sample container 350 as described above with respect to the sample container 14. The sample container 350 is then used with the mechanism similar to the mechanism 12 of FIG. 1. The position of the spring member 30 and the length of the depression 38 is adjusted to accommodate the greater length of the sample container 350. Also, a groove is formed in a cam similar to the cam 78 to add additional horizontal and vertical displacements to wipe or blot the lower end of the elongated portion 126 within the slot 364 after the elongated portion 126 is removed from the sample reservoir 360. The sample container 350 is then again displaced vertically, horizontally and vertically so as to immerse the end of the elongated portion 126 within the control 372. In this fashion, the sample container 350 not only provides calibrator 354 for use with the electrode assembly 16 but also a control 372 to verify or confirm the performance of the electrode assembly 16.

Other modifications to the present invention will be readily apparent to those skilled in the art. For example, the electrode assembly 16 may be modified to form other electrochemically active assemblies by the use of ion selective electrodes selective for other analytes such as, for example, lithium, pH, ionized calcium, and magnesium, or enzyme reactive electrodes for the measurement of glucose and cholesterol. Furthermore, more than two ion selective electrodes may be disposed on the elongated portion 126 on the electrode assembly 16 so that more than two analytes may be measured simultaneously. Furthermore, a sensing assembly similar to the electrode assembly 16 using other sensing techniques will be readily apparent to those skilled in the art, such as so-called "optodes" which use fiberoptic sensors to detect fluorescence changes within a sample fluid. Also, the electrode assembly 16 may be moved by a cam with respect to the sample container 14 while achieving the same result in the essentially the same way as described above.

Thus, the present invention provides a simple and inexpensive approach to analyte measurement heretofore unknown in the art. Analyses performed with the present invention are fast and simple as well as automated, enabling a user of a present invention to attend to other duties while an analysis is being performed. As little as 80 ul of sample is sufficient to fill the sample reservoirs 208 and 360 of the respective sample containers 14 and 350, thus providing a system adapted for pediatric as well as geriatric use. The present invention enables the design of a small, portable analyzer, low in cost and simple in use and operation.

EXAMPLES

Example 1

Sodium Ion Selective Membrane

|  | % by weight |
|---|---|
| BIS (12-crown-4) (Dojindo Labs) | 2 |
| PVC powder (Fluka Chemical) | 28.5 |
| di-isodecyl adipate (Scientific Polymer Products P-140) | 69 |
| potassium tetrakis (4-chlorophenyl) borate (Fluko Chem. #60591, purum grade) | 0.5 |

Example 2

Potassium Ion Selective Membrane

|  | % by weight |
|---|---|
| Valinomycin | 1.4 |
| di-isodecyl adipate | 69 |
| PVC powder | 29.6 |

Example 3

Reference Gel Composition

|  | % by weight |
|---|---|
| Carboxy Methyl Cellulose (CMC) | 4.7% |
| NaCl | 0.5% |
| NaHCO$_3$ | 0.38% |
| KCl | 0.03% |
| Trizma base | 3.6% |

|  | % by weight |
|---|---|
| H$_2$O | Balance |

Example 4

Conditioning, Storage Gel Composition

|  | % by weight |
|---|---|
| ME Agarose | 1% |
| NaCl | 0.5% |
| NaHCO$_3$ | 0.38% |
| KCl | 0.03% |
| Trizma Base | 3.6% |
| H$_2$O | Balance |

The present invention is not to be limited to the particular embodiments disclosed herein but is to be accorded the full scope of the appended claims and all equivalents thereof.

We claim:

1. An ion selective electrode assembly comprising:
a substrate;
a plurality of conductive members deposited upon the substrate;
an insulating layer applied over the conductive members and fixed to the substrate, the insulating layer including openings exposing at least a portion of each conductive member;
ion selective means deposited over one of the conductive members exposed by the insulating layer;
reference electrode means deposited over a second one of the conductive members exposed by the insulating layer;
a well formed by the substrate and insulating layer, the well including the reference electrode means;
a reference medium disposed in such well and in contact with the reference electrode means; and
a cover disposed over the well for sealing the reference medium within the well.

2. An electrode assembly as in claim 1 wherein the insulating layer is heat laminated to the substrate.

3. An electrode assembly as in claim 1 wherein the volume of the well covered by the a cover is about 100 microliters.

4. An electrode assembly as in claim 1 wherein the substrate comprises a first portion into which the well is formed and a second elongated portion upon which the ion selective means is deposited.

5. An electrode assembly as in claim 4 wherein the elongated portion includes an end in the form of a pointed tip.

6. An electrode system including the electrode assembly of claim 4 and a sleeve adapted to receive the second elongated portion of the electrode assembly, the sleeve including a reservoir holding conditioning medium means.

7. An electrode assembly in claim 1 wherein the substrate is formed from rigid PVC sheet material.

8. An ion selective electrode assembly comprising:
a body including a rectangular portion and an elongated portion, the body comprising a substrate formed from sheet PVC material, a plurality of conductive members deposited upon the substrate, and an insulting layer heat laminated to the substrate over the conductive members, the insulating layer including openings exposing at least a portion of each conductive member, a first of such openings being disposed on the elongated portion and a second of such openings being disposed on the rectangular portion;

ion selective means deposited over the portion of the conductive members exposed by the first opening;

reference electrode means deposited over the portion of the conductive members exposed by the second opening;

a well formed by the substrate and insulating layer, the well including the reference electrode means;

a reference medium disposed in such well and in contact with the reference electrode means; and a cover disposed over the well for sealing the reference medium within the well.

9. An electrode assembly as in claim 8 wherein the volume of the well covered by the cover is about 100 microliters and the elongated portion includes an end in the form of a pointed tip.

10. An electrochemically active electrode assembly comprising:
a substrate;
a plurality of conductive members deposited upon the substrate;
an insulating layer applied over the conductive members and fixed to the substrate, the insulating layer including openings exposing at least a portion of each conductive member;
electrochemically active means deposited over one of the conductive members exposed by the insulating layer;
reference electrode means deposited over a second one of the conductive members exposed by the insulating layer;
a well formed by the substrate and insulating layer, the well including the reference electrode means;
a reference medium disposed in such well and in contact with the reference electrode means; and
a cover disposed over the well for sealing the reference medium within the well.

11. A sample container comprising:
first and second fluid reservoirs;
absorbing means proximate the first and second fluid reservoirs, the reservoirs and absorbing means forming an integral unit;
a third fluid reservoir proximate the second fluid reservoir and a notch formed between the second and third fluid reservoirs.

12. A sample container as in claim 11 wherein the absorbing means includes a slot and a fluid absorbing material retained within the slot.

13. A sample container as in claim 12 wherein the slot is intermediate the first and second reservoirs.

14. A sample container as in claim 13 wherein the sample container includes a liquid retained within the first reservoir and a seal covering the first reservoir and retaining the liquid therein.

15. A sample container as in claim 14 wherein the liquid is a calibrator liquid adapted for use with an ion selective electrode.

16. A sample container as in claim 11 wherein the sample container includes a third fluid reservoir proximate the second fluid reservoir and a second absorbing means intermediate the second and third fluid reservoirs.

17. A sample container as in claim 16 wherein the sample container includes a first liquid retained within the first reservoir and a second liquid retained within the third reservoir and sealing means covering the first and third reservoirs for retaining the liquids disposed therein.

18. A sample container as in claim 17 wherein the first liquid is a calibrator liquid adapted for use with an ion selective electrode and the second liquid is a control liquid for use with an ion selective electrode.

19. A sample container as claimed in claim 11, wherein there is only a single in-line configuration.

20. A sample container as claimed in claim 11 wherein the reservoirs and absorbing means are contained in a substantially rectangular plane.

21. An sample container as claimed in claim 11 wherein the notch act as a spillway between the second and third reservoirs.

22. An analytical kit comprising an electrode assembly and a sample container;
the electrode assembly comprising a body including a rectangular portion and an elongated portion, a plurality of conductive members deposited upon the substrate, and an insulating layer fixed to the substrate over the conductive members, the insulating layer including openings exposing at least a portion of each conductive member, a first of such openings being disposed on the elongated portion and a second of such openings being disposed on the rectangular portion; ion selective means deposited over the portion of the conductive members exposed by the first opening; reference electrode means deposited over the portion of the conductive members exposed by the second opening; an well formed by the substrate and insulating layer, the well including the reference electrode means; a reference medium disposed in such well and in contact with the reference electrode means; and a cover disposed over the well for sealing the reference medium within the well;
the sample container comprising a first and second fluid reservoir adapted to receive the elongated portion of the electrode assembly, the sample container further including a slot intermediate the first and second reservoirs and an absorbing material retained within the slot, the slot being sized to receive the elongated portion of the electrode assembly.

23. An analytical apparatus for use with a sensing assembly and a sample container comprising:
support means for receiving and removably retaining the sensing assembly;
a support table adapted to removably retain the sample container;
pivot means for pivoting the support table about horizontal and vertical axes;
a cam including a cam surface;
means for engaging the cam surface and coupling motion described by the cam surface to the support table; and
means for driving the cam.

24. An apparatus as in claim 23 wherein the cam surface describes a path adapted to displace the support table vertically and horizontally with respect to the support means.

25. An analytical system comprising:
the sensing assembly comprising a body including an elongated portion, and sensing means disposed on the elongated portion;

the sample container comprising a first and second fluid reservoir adapted to receive the elongated portion of the sensing assembly, the sample container further including a slot intermediate the first and second reservoirs and an absorbing material retained within the slot, the slot being sized to receive the elongated portion of the sensing assembly; and a transport mechanism including support means for receiving and removably retaining the sensing assembly; a support table adapted to removably retain the sample container; pivot means for pivoting the support table about horizontal and vertical axes; a cam including a cam surface; means for engaging the cam surface and coupling motion described by the cam surface to the support table; and mean for driving the cam.

26. An analytical system as in claim 25 wherein the cam surface describes a path adapted to move the sample container with respect to the sensing assembly to sequentially insert the elongated portion into the first reservoir, into the slot, and into the second reservoir.

27. A sample container comprising:
a first and second fluid reservoir;
absorbing means proximate and separate from the first and second fluid reservoir;
a third fluid reservoir proximate the second fluid reservoir, the reservoirs and absorbing means being in a substantially in-line configuration; and
a notch formed between the second and third reservoirs.

28. A sample container as in claim 27 wherein the sample container includes a liquid retained within the first reservoir and a seal covering the first reservoir and retaining the liquid therein.

29. A sample container as in claim 28 wherein the liquid is a calibrator liquid for use with an ion selective electrode.

30. A sample container as in claim 27 wherein the sample container includes a first liquid retained within the first reservoir and a second liquid retained within the third reservoir and sealing means covering the first and third reservoirs for retaining the liquids disposed therein.

31. A sample container as claimed in claim 27 wherein there is only a single in-line configuration.

32. A sample container as claimed in claim 27 wherein the reservoirs and absorbing means are contained in a substantially rectangular plane.

33. An analytical kit comprising a sensing assembly and a sample container;
the sensing assembly comprising a body including an elongated portion, and sensing means disposed on the elongated portion;
the sample container comprising a first and second fluid reservoir adapted to receive the elongated portion of the sensing assembly, the sample container further including a slot intermediate the first and second reservoirs and an absorbing material retained within the slot, and separate from the reservoirs, the reservoirs and the absorbing material being in a substantially in-line configuration, the slot being sized to receive the elongated portion of the sensing assembly, wherein the elongated portion includes a pointed tip and the sample container includes a seal covering one of the first and second reservoirs adapted to be pierced by the tip of the elongated portion upon insertion of the elongated portion into the sealed reservoir.

34. An analytical kit as claimed in claim 33 wherein there is only a single in-line configuration.

35. An analytical kit as claimed in claim 33 wherein the reservoirs and slot are contained in a substantially rectangular plane.

* * * * *

UNITED STATES PATENT AND TRADEMARK OFFICE
CERTIFICATE OF CORRECTION

PATENT NO. : 4,889,613

DATED : December 26, 1989

INVENTOR(S) : Mc Neal, Jack D., et al.

It is certified that error appears in the above-identified patent and that said Letters Patent is hereby corrected as shown below:

Column 5, line 39 reads -- The substrate layer 1130 is -- should read -- The substrate layer 130 is -- .

Column 8, line 16 reads -- that as been -- should read -- that has been -- .

(Claim 8) Column 14, line 67 reads -- an insulting layer -- should read -- an insulating layer -- .

Signed and Sealed this

Twenty-ninth Day of September, 1992

Attest:

DOUGLAS B. COMER

*Attesting Officer*   *Acting Commissioner of Patents and Trademarks*